(12) United States Patent
Flippin

(10) Patent No.: US 9,744,192 B2
(45) Date of Patent: Aug. 29, 2017

(54) METHODS OF TREATING CHRONIC RHINOSINUSITIS

(71) Applicant: Lee A. Flippin, Woodside, CA (US)

(72) Inventor: Lee A. Flippin, Woodside, CA (US)

( * ) Notice: Subject to any disclaimer, the term of this patent is extended or adjusted under 35 U.S.C. 154(b) by 0 days.

(21) Appl. No.: 14/726,156

(22) Filed: May 29, 2015

(65) Prior Publication Data
US 2016/0271173 A1  Sep. 22, 2016

Related U.S. Application Data

(60) Provisional application No. 62/133,920, filed on Mar. 16, 2015.

(51) Int. Cl.
| | |
|---|---|
| A61K 33/22 | (2006.01) |
| A61K 47/02 | (2006.01) |
| A61K 9/08 | (2006.01) |
| A61M 15/08 | (2006.01) |
| A61K 9/00 | (2006.01) |

(52) U.S. Cl.
CPC ............ *A61K 33/22* (2013.01); *A61K 9/0043* (2013.01); *A61K 9/08* (2013.01); *A61K 47/02* (2013.01); *A61M 15/08* (2013.01)

(58) Field of Classification Search
CPC .......... A61K 33/22; A61K 47/02; A61K 9/08; A61K 9/0043; A61M 15/08
See application file for complete search history.

(56) References Cited

U.S. PATENT DOCUMENTS

| | | | | |
|---|---|---|---|---|
| 5,135,952 A * | 8/1992 | Ohmori | ............... | C07K 5/0215 514/547 |
| 6,232,343 B1 * | 5/2001 | Ikari | .................. | A61K 31/5585 514/530 |
| 2008/0287395 A1* | 11/2008 | Ghosh | ...................... | A61L 2/18 514/77 |

FOREIGN PATENT DOCUMENTS

WO    WO 2007/134055 A1    11/2007

OTHER PUBLICATIONS

Pur-Wash water solution monograph (Niagara Pharmaceuticals, Inc.; Revised Sep. 2011).*
Ward et al., "Molal Volume of Aqueous Boric Acid-Sodium Chloride Solutions," Journal of Solution Chemistry, 1974; 3(6): pp. 431-444.*
Bachert, Claus et al. (2014) ICON: chronic rhinosinusitis. World Allergy Organ J 7(1):25.
Fokkens, W.J. et al. (2012) European position paper on rhinosinusitis and nasal polyps 2012. Rhinology 50(Suppl 23):1-298.
Kern, Robert C. et al. (2008) Perspectives on the etiology of chronic rhinosinusitis: An immune barrier hypothesis. Am J. Rhinol 22(6):549-559.
Cain, Rachel B. and Lal, Devyani (2013) Update on the management of chronic rhinosinusitis. Infect Drug Resist 6:1-14.
Newton, Jonathan Ray and Ah-See, Kim Wong (2008) A review of nasal polyposis. Ther Clin Risk Manag 4(2):507-512.
Kaplan, Alan (2013) Canadian guidelines for chronic rhinosinusitis. Can Fam Physician 59(12):1275-1281.
Chalermwatanachai, Thanit et al. (2015) The microbiome of th eupper airways: focus on chronic rhinosinusitis. World Allergy Organ J 8(1):3.
Hamilos, Daniel (2014) Host-microbial interactions in patients with chronic rhinosinusitis. J Allergy Clin Immunol 33(3):640-653.
Lim, Mingyann et al. (2008) Topical antimicrobials in the management of chronic rhinosinusitis: A sstematic review. Am J Rhinol 22(4)381-389.
Huang, Alice and Govindaraj, Satish (2013) Topical therapy in the management of chronic rhinosinusitis. Curr Opin Otolaryngol Head Neck Surg 21(1):31-38.
Kennedy, Joshua and Borish, Larry (2013) Chronic rhinosinusitis and antibiotics: The good, the bad, and the ugly. Am J Rhinol Allergy 27(6):467-472.
Cleland, Edward John et al. (2014) Probiotic manipulation of the chronic rhinosinusits microbiome. Int Forum Allergy Rhinol 4(4):309-314.
Mukerji, S.S. et al. (2009) Probiotics as adjunctive treatment for rhinosinusitis: A randomized controlled trial. Otoiaryngol Head Neck Surg 140(2):202-208.
Goggin, Rachel et al. (2014) Colloidal silver: a novel treatment fo *Staphylococcus aureaus* biofilms? Int Forum Allergy Rhinol 4(3):171-175.
Chui, Alexander G. et al. (2008) Baby shampoo nasal irrigations for the symptomatic post-functional endoscopic sinus surgery patient. Am J Rhinol 22(1):34-37.
Casale, Manuele et al. (2014) The potential role of hyaluronan in minimizing symptoms and preventing axacerbations of chronic rhinosinusitis. Am J Rhnol allergy 28(4):345-48.
Kilty, Shaun J. et al. (2011) Methylgloxal: (active agent of Manuka honey) in vitro activity against bacterial biofilms. Int Forum Allergy Rhinol 1(5):348-350.
Weissman, Joshua D. et al. (2011) Xylitol nasal irrigation in th emanagement of chronic rhinosinusitis: a pilot study. Laryngoscope 121(11):2468-72.
Van Den Berg, Jelle W.G. et al. (2014) Limited evidence: higher efficacy of nasal saline irrigation over nasal saline spray in chron . . . Otolaryngol Head Neck Surg 150(1)16-21.
Ural, A. et al. (2009) Impact of isotonic and hypertonic saline solutions on mucociliary activity in various nasal pathologies: clinical study. J Laryngol Otol 123(5):517-21.

(Continued)

*Primary Examiner* — Sreeni Padmanabhan
*Assistant Examiner* — Jody Karol

(57) ABSTRACT

The present invention provides methods of treating chronic rhinosinusitis that comprise administering a formulation of boric acid to the nasal and paranasal cavities of a patient in need. The present invention also provides for the use of a formulation comprising boric acid for the treatment of chronic rhinosinusitis.

2 Claims, No Drawings

(56) References Cited

OTHER PUBLICATIONS

Ansari, N,N. et al. (2012) A randomized, double-blind clinical trial comparing the effects of continuous and pulsed ultrasound in patient . . . Physiother Theory Pract 28(2):85-94.
Young, D. et al. (2010) Therapeutic ultrasound as treatment for chronic rhinosinusitits: preliminary observations. J Laryngol Otol 124(5):495-499.
Schmidt et al. (2010) Boric acid distrubs cell wall synthesis in *Saccharomyces cerevisiae*. Int J Microbiol 2010:930465.
De Seta, Francesco et al. (2009) Antifungal mechanisms supporting boric acid therapy of Candida vaginitis. J Antimicrob Chemother 63(2):325-26.
Appannanavar, S.B. et al. (2013) Evaluation of commercial boric acid containing vials for urine culture: low risk of contamination . . . Indian J Pathol Microbiol 56(3):261-64.
Brodie, J. and Porter, I.A. (1971) Boric-acid preservation of urine samples. Lancet 1(7690):133.
Meers, P.D. and Chow, C.K. (1990) Bacteriostatic and bactericidal actions of boric acid against bacterial and fungi commonly found in urine. J Clin Pathol 43(6):484-87.

\* cited by examiner

METHODS OF TREATING CHRONIC RHINOSINUSITIS

CROSS REFERENCE TO RELATED APPLICATIONS

This application claims the benefit under 35 U.S.C. §119(e) of U.S. Provisional Application 62/133,920, filed Mar. 16, 2015, which application is hereby incorporated by reference in its entirety.

FIELD OF THE INVENTION

The present invention relates to methods for treating chronic rhinosinusitus.

BACKGROUND

Chronic Rhinosinusitis (CRS) is a persistent symptomatic inflammation of the nasal and paranasal sinuses characterized by at least 8-12 weeks of two or more symptoms selected from nasal congestion or blockage, anterior or posterior nasal discharge, facial pressure or pain, and reduction or loss of smell. CRS is further categorized based on the presence or absence of nasal polyps (CRS without nasal polyps, CRSsNP; or CRS with nasal polyps, CRSwNP). CRSsNP is frequently associated with facial pressure or pain, whereas CRSwNP is frequently associated with a reduced ability to smell and detect odors (hyposmia). (Bachert et al. (2014) World Allergy Organ J 7(1):25; European Position Paper on Rhinosinusitis and Nasal Polyps (EPOS 2012).)

CRS is considered a public health problem having a significant social and economic impact. CRS has been variously estimated to affect from 5% to 15% of the general population, and overall annual economic burden of CRS in the United States alone has been estimated to be $22 billion in 2014. (Bachert et al., supra; Smith et al. (2015) Laryngoscope doi: 10.1002/lary.25180.) Although not considered a life-threatening disease, the measurable impact of CRS on quality of life is profoundly negative, including increased sleep dysfunction, anxiety and depression in patients having CRS. (See, e.g., Alt et al. (2013) Int Forum Allergy Rhinol 3(11):941-949; Katotomichelakis et al. (2014) Int J Psychiatry Med 48(2):83-94.)

While the exact etiology of CRS has not been clearly defined, a number of hypotheses have been considered. The mucosa lining the nasal and paranasal cavities is the interface with inhaled irritants, aero-allergens, commensal organisms, and pathogens. Because of the importance of the epithelium as a mediator of immune defense, it has been suggested that defects in a broad set of epithelium-related genes could contribute to a dysfunctional immune response to environmental agents in patients with CRS. (Kern et al. (2008) Am J Rhinol 22(6):549-559.) Diminished host defense may contribute to local microbial proliferation fostering the development of CRS. While the role of microbes as causative agents in CRS is not clear, bacterial and/or fungal infection and biofilms may contribute to the propagation of CRS. (Cain and Lal (2013) Infect Drug Resist 6:1-14.) Endoscopic surgery is the only known treatment option for effective removal of obstructive nasal polyps from CRSwNP patients; however, estimated polyp recurrence rates are unacceptably high even with use of chronic corticosteroid therapy. (Wynn and Har-El (2004) Laryngoscope 114(5):811-813; Newton and Ah-See (2008) Ther Clin Risk Manag 4(2):507-512.) Effective preventative therapy against polyposis in CRS disease, before and after surgical intervention, clearly remains an important unmet medical need.

Despite many decades of world-wide effort toward discovery of therapeutic approaches against CRS, effective treatment options for this disease remain limited in scope and largely inadequate. While both CRSwNP and CRSsNP are typically treated with intranasal corticosteroids (INS), second line antibiotics are often recommended in CRSsNP but are only recommended in CRSwNP when symptoms indicate infection (pain or purulence). Saline irrigation and oral steroids may also be recommended when appropriate. (Kaplan (2013) Can Fam Physician 59(12):1275-1281.) Within the past two decades, however, and particularly since the advent of the NIH Human Microbiome Project in 2008, a large body of compelling research has linked inappropriate microbial colonization of the paranasal mucosa and a consequent state of chronic immuno-inflammatory activation to the distinctive pathophysiology of CRS. (Chalermwatanachai et al. (2015) World Allergy Organ J 8(1):3; Hamilos (2014) J Allergy Clin Immunol 33(3):640-653.) While various symptoms of CRS have all been reported to respond favorably to chronic INS therapy, it is clear that INS therapy can do little to resolve the underlying cause of microbial-related CRS disease.

To date, no effective means of restoring host-microbial balance and mitigating disease in patients with CRS has been found. A large number of systemic and topical bactericidal or fungicidal drugs have been explored in the context of CRS disease, often showing very good short-term efficacy for reduction of microbial density in the paranasal mucosa and concomitant alleviation of CRS clinical symptoms. (See, e.g., Kaplan, supra; Lim et al. (2008) Am J Rhinol 22(4):381-389; Huang and Govindaraj (2013) Curr Opin Otolaryngol Head Neck Surg 21(1):31-38.) Long-term use of antibiotics is not recommended, however, due to concerns over the danger of promoting expansion of resistant bacteria. (Kennedy and Borish (2013) Am J Rhinol Allergy 27(6): 467-472.) Alternatively, clinical use of various probiotic agents and other "microbiome rebalancing" strategies has been suggested for CRS disease. (Cleland et al. (2014) Int Forum Allergy Rhinol 4(4):309-314; Mukerji et al. (2009) Otolaryngol Head Neck Surg 140(2):202-208.)

A number of alternative therapies have been postulated for CRS disease including intranasal irrigations with colloidal silver, surfactant solutions derived from commercial baby soap products, sodium hyaluronate, methylglyoxal, xylitol solution, and isotonic or hypertonic saline. (Goggin et al. (2014) Int Forum Allergy Rhinol 4(3):171-175; Chiu et al. (2008) Am J Rhinol 22(1):34-37; Casale et al. (2014) Am J Rhinol Allergy 28(4):345-348; Kilty et al. (2011) Int Forum Allergy Rhinol 1(5):348-350; Weissman et al. (2011) Laryngoscope 121(11):2468-72; van den Berg et al. (2014) Otolaryngol Head Neck Surg 150(1):16-21; Ural et al. (2009) J Laryngol Otol 123(5):517-21.) Ultrasound treatment to disrupt bacterial biofilm in CRS has also been suggested. (Ansari et al. (2012) Physiother Theory Pract 28(2):85-94; Young et al. (2010) J Laryngol Otol 124(5): 495-499.)

There remains a need in the art for an effective treatment of chronic rhinosinusitis. The present invention provides an efficacious treatment to reduce the symptoms of chronic rhinosinusitis and improve the quality of life of those suffering from CRS. The invention also provides for the use of a boric acid formulation for the treatment of chronic rhinosinusitis in a patient in need.

SUMMARY OF THE INVENTION

The present invention provides methods of treating chronic rhinosinusitis comprising the administration of a volume of a formulation of boric acid to the nasal and paranasal cavities of a patient in need. The present invention also provides for use of a formulation comprising boric acid for the treatment of chronic rhinosinusitis in a subject in need.

In either the method or use described and claimed herein, the formulation comprises boric acid in an amount (weight per volume, w/v) from about 1.0-4.0%, particularly from about 1.0-2.5%. In particular embodiments, the formulation comprises boric acid in an amount of about 2.0% (w/v).

In various embodiments, the formulation additionally comprises a saline solution, wherein the concentration (w/v) of sodium chloride (NaCl) in water is from about 0.5-1.2%. In a particular embodiment the concentration of sodium chloride in water is 0.9% (w/v), that is, isotonic saline. In one embodiment, the formulation comprises about 2% (w/v) of boric acid in a saline solution having about 0.9% (w/v) of sodium chloride in water.

The formulation may be of a pH that is a natural result of formulating the desired amount of boric acid in a saline solution.

In various embodiments, the method of administering the boric acid formulation comprises applying a volume of the formulation into each nare of the subject in need in a manner sufficient to penetrate the nasal and paranasal cavities. The volume of the formulation may be administered by any appropriate means known to those skilled in the art and include, but are not limited to, douching, nebulization, atomization, inhalation, irrigation, spray, drops, or insufflations. In particular embodiments, a volume of the formulation is administered by drops into each nare. In other particular embodiments, the volume of the formulation is applied by spray into each nare.

In a specific embodiment, the formulation is a sterile, aqueous isotonic suspension or solution of boric acid. In another specific embodiment, the method comprises administering a volume of a formulation of sterile, aqueous isotonic suspension of boric acid intranasally to the nasal-paranasal mucosa via spray pump. In embodiments of the invention, the various methods of administration may be and often are accompanied by maneuvering the head, and thereby the nasal and paranasal cavities, in a manner sufficient to distribute the formulation throughout the nasal and paranasal cavities. The method also may and often does include a subsequent step of clearing the nasal and paranasal cavities of excess formulation by expectoration and/or exsufflation.

In various embodiments, the volume of the formulation administered into each nare may vary but in all cases should be a volume sufficient to coat the nasal and paranasal cavities. In particular embodiments, the volume administered to each nare is about 1-2 mL. Administration is generally based on need and may be repeated several times per day while symptoms are present. In particular embodiments, formulation is administered to the subject in need 1-3 times per day.

In all embodiments of the invention, the subject in need is a subject having symptoms consistent with chronic rhinosinusitis. In some embodiments, the subject has been diagnosed as having chronic rhinosinusitis. In some embodiments, the subject having chronic rhinosinusitis may also have nasal polyps (CRSwNP). In other embodiments, the subject having chronic rhinosinusitis does not have nasal polyps (CRSsNP). In some embodiments, the chronic rhinosinusitis is microbial-related CRS. In particular embodiments, the chronic rhinosinusitis is bacterial-related. In some embodiments, the chronic rhinosinusitis is fungal-related.

A present invention further provides a formulation comprising boric acid for use in treating chronic rhinosinusitis. In various embodiments, the formulation comprises about 1.0-4.0% (w/v) of boric acid, more particularly about 2.0% (w/v) of boric acid. In some embodiments, the formulation further comprises a saline solution having about 0.5-1.2% (w/v) of sodium chloride in water, in particular a saline solution having about 0.9% (w/v) of sodium chloride in water.

These and other embodiments of the subject invention will readily occur to those of skill in the art in light of the disclosure herein, and all such embodiments are specifically contemplated.

DETAILED DESCRIPTION OF THE INVENTION

Before the present formulations and methods are described, it is to be understood that the invention is not limited to the particular methodologies, protocols, and reagents described, as these may vary. It is also to be understood that the terminology used herein is intended to describe particular embodiments of the present invention, and is in no way intended to limit the scope of the present invention as set forth in the appended claims.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items. It must be noted that as used herein and in the appended claims, the singular forms "a," "an," and "the" include plural references unless context clearly dictates otherwise.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure.

The practice of the present invention will employ, unless otherwise indicated, conventional methods of chemistry, biochemistry, molecular biology, cell biology, genetics, immunology and pharmacology, within the skill of the art. Such techniques are explained fully in the literature. See, e.g., Gennaro, A. R., ed. (1990) Remington's Pharmaceutical Sciences, 18th ed., Mack Publishing Co.; Hardman, J. G., Limbird, L. E., and Gilman, A. G., eds. (2001) The Pharmacological Basis of Therapeutics, 10th ed., McGraw-Hill Co.; Colowick, S. et al., eds., Methods In Enzymology, Academic Press, Inc.; Weir, D. M., and Blackwell, C. C., eds. (1986) Handbook of Experimental Immunology, Vols. I-IV, Blackwell Scientific Publications.

The section headings are used herein for organizational purposes only, and are not to be construed as in any way limiting the subject matter Definitions The terms "disorders," "diseases," and "conditions" are used inclusively herein and refer to any condition deviating from normal.

The terms "treating," "treatment" and the like, are used herein to mean administering a therapy to a patient in need thereof.

An "effective amount" of a compound or formulation is an amount sufficient to bring about the desired result in a treated subject, for example, an amount sufficient to treat chronic rhinosinusitis in a subject in need. The effective amount can vary depending upon the particular formulation, the nature or severity of the condition being treated, the age, weight, etc. of the subject being treated, the route of administration or formulation of the compound, and the dosing regimen, among other things. An effective amount can readily be determined by one skilled in the medical arts.

The Invention

The present invention provides methods of treating chronic rhinosinusitis that comprise administering a formulation of boric acid to the nasal and paranasal cavities of a patient in need. The present invention also provides for the use of a formulation comprising boric acid for the treatment of chronic rhinosinusitis.

Regardless of any palliative benefits of anti-inflammatory therapy in CRS, the present inventor has found that CRS, and in particular microbial-related CRS, fundamentally requires a therapeutic approach that can safely and conveniently reduce inappropriate bacterial or fungal colonization of the human host's paranasal mucosa with minimal and tolerable side-effects.

The present invention is based on the use of a reversible, non-specific microbiostatic agent, which, unlike bactericidal or fungicidal enzyme inhibitors, may not readily induce adaptive resistance in microbes. Irrigation of microbe-colonized tissues with a reversible microbiostatic agent followed by a wash-out or dilution of the agent to sub-effective levels allows the remaining wild-type bacteria and/or fungi to continue propagating without significant pressure to acquire drug resistance.

Although the invention is not limited to any particular mechanism of action (MOA), the non-specific microbiostatic agent may target such fundamental molecular properties of microbial cell walls that acquisition of specific resistance factors is difficult and ineffective. For example, the presence of either a thick (Gram-positive) or thin (Gram-negative) peptidoglycan sacculus is intrinsic to the bacteria of pathogenic importance in humans. The highly-conserved repeating disaccharide unit, β-(1,4)-N-acetyl-D-glucosamine (GlcNAc)-O—N-acetylmuramic acid (MurNAc), comprises the helical chain of peptidoglycan which is further structurally modified by short crosslinking peptides. Each disaccharide unit of a peptidoglycan strand contains three hydroxyl (—OH) groups that contribute to the fundamental properties of the helical polymer-polar R—OH groups act individually as either hydrogen-bond donors or acceptors to create, in aggregate, functionally important secondary structure within the peptidoglycan helix. The normal conformation, porosity, flexibility, and polarity properties of the bacterial peptidoglycan surface could be significantly disrupted by reversible complexation of the free hydroxyl groups of peptidoglycan disaccharide thus leading to temporary growth arrest.

Similarly, α- and β-glucan polysaccharides, GlcNAc polymer (chitin), and glycoproteins modified with O- and N-linked saccharides are the major components of fungal cell wall surfaces. Thus, non-specific and reversible complexation of fungal cell-surface glycoconjugates and polysaccharides by a non-specific microbiostatic agent might similarly lead to non-lethal growth arrest in fungal pathogens.

Additionally, a non-specific microbiostatic agent may target and interfere with mechanisms utilized by microbial agents to adhere to and colonize the nasal and paranasal cavities. For example, because adhesion is a crucial survival factor it is not surprising that most microbial pathogens employ complex strategies against their hosts, exploiting multiple adhesion mechanisms. For example, bacterial lectins bind with high specificity to cell surface saccharide motifs creating strong adhesion bonds between pathogen and host. The basic concept of blocking lectin-saccharide interactions as an approach to preventing bacterial adhesion and infection has been demonstrated in animal models. A therapeutic agent that could reversibly and non-selectively complex with host epithelial cell polysaccharides might effectively block lectin-saccharide bacterial adhesion without causing either bacterial or host-cell death.

Biofilm formation is also a common and very effective strategy for microbial adhesion to host cell surfaces. Typical biofilms are complex mixtures of protein, polysaccharide, nucleic acids, and lipids that provide a mechanically stable extracellular matrix in support of microbial colonization. A non-specific polysaccharide-complexing agent might significantly destabilize biofilm matrices making them less hospitable microbial habitats and rendering the disrupted matrix more susceptible to mucociliary expulsion.

Boric Acid

Any reference to "boric acid" herein includes the various sources and forms described below.

Boric acid, $B(OH)_3$, found in nature as the mineral sassolite, is an extremely weak acid ($pK_a$=9.24) with good water solubility (0.47 g/mL@20° C.). In aqueous solution at pH=7.4, free boric acid is the major component of a rapidly established equilibrium with hydronium borate:

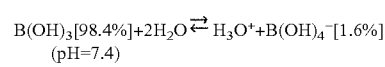
$$B(OH)_3[98.4\%]+2H_2O \rightleftarrows H_3O^++B(OH)_4^-[1.6\%]$$
(pH=7.4)

(See, e.g., Woods (1994) Environ Health Perspect 102(Suppl 7):5-11.)

Borax, $Na_2[B_4O_5(OH)_4]$, found in nature as the mineral colemanite, is also in pH-dependent equilibrium with boric acid and borate in aqueous solutions. Thus, aqueous boric acid-borax mixtures form a well-known buffer system that is useful over the pH range=7.4-9.7;

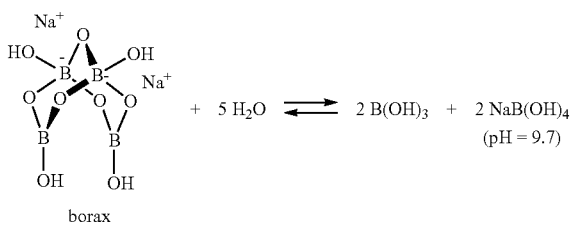

$$\text{borax} + 5\,H_2O \rightleftharpoons 2\,B(OH)_3 + 2\,NaB(OH)_4 \quad (pH = 9.7)$$

(See, e.g., Coddington and Taylor (1989) J Coord Chem 20(1):27-38)

Bacteriostatic and Fungistatic Properties of Boric Acid

Aqueous solutions of boric acid or borax are known to rapidly and reversibly form borate ester complexes with many hydroxyl-containing organic compounds, especially monosaccharides (e.g., glucose, mannose, galactose, fructose, rhamnose, xylose, maltose, and lactose) and polysaccharides (Deuel et al. (1948) Nature 161(4081):96.) Depending on the number and conformation of free hydroxyl groups in the saccharide or polysaccharide structure, sugar borate esters may form in a variety of stoichiometries including well-known 2:1 sugar:borate Spiro complexes. In dilute aqueous solution, susceptible polysaccharides react with boric acid to give borate-polysaccharide chain complexes that may cross-link to cause three-dimensional network formation and rapid gelification of the mixtures. In this context it is provocative that 2-3% aqueous boric acid has been observed to cause marked agglutination of *Bacillus shiga-kruse* (aka: *Shigella dysenteriae*) in agar culture. (Lopatkin (1940) Zhurnal Mikrobiologii, Epidemiologii i Immunobiologii 7:30-32) *S. dysenteriae* is a Gram-negative species known to produce cell-wall polysaccharides containing a high proportion of boric acid-reactive rhamnose. It was noted in this work, "No other acid, inorganic or organic, gave this reaction." Boric acid has also been shown to alter the morphology of living *Saccharomyces cerevisiae* cells. (Schmidt et al. (2010) Int J Microbiol 2010; 2010:930465.)

An in vitro study of boric acid against cultured Candida albicans demonstrated that 1% aqueous boric acid showed complete growth inhibition against 45 of the 46 fluconazole-susceptible strains tested and 24 of the 25 fluconazole-resistant strains tested. Using a focus set of six *C. albicans* strains the authors of this study were able to convincingly eliminate pH as a primary basis for the fungistatic effects of boric acid. No sign of sudden physical membrane damage was apparent and membrane integrity decreased only slightly during 24 hour exposure to 1% boric acid. (De Seta et al. (2009) J Antimicrob Chemother 63(2):325-36.) This same study reported that 2.5% boric acid was sufficient for complete growth inhibition of 17 of 17 bacterial strains tested including *Staphylococcus aureus* (2 strains), *Enterococcus faecalis, Staphylococcus saprophyticus, Staphlyococcus epidermis, Bacillus* sp., *Streptococcus pyogenes, Streptococcus agalactiae, Citrobacter freundii, Enterobacter cloacae, E. coli* (2 strains), *Klebsiella pneumonia, Shigella* sp., *Proteus* sp., *Salmonella* sp., and *Serratia* sp. (De Seta et al., supra.)

Microbial growth in urine samples while in transit to a pathology laboratory is known to lead to significant time-dependent false positive results in medically important assays. However, microbiocidal treatment of such samples is untenable because the pathogenic species present in them subsequently need to be grown in culture for identification. Boric acid, 1.8-2%, has been known and used for decades as an efficient microbiostatic agent for transportation of urine samples containing a wide range of bacterial and fungal pathogens. (Appannanavar et al. (2013) Indian J Pathol Microbiol 56(3):261-264; Brodie and Porter (1971) Lancet 1(7690):133.) In controlled experiments using 17 bacteria and fungi, the integrity of initial bacterial or fungal counts was maintained for all human pathogens studied for up to 24 hours at 24° C. (Meers and Chow (1990) J Clin Pathol 43(6):484-487.) When subsequently diluted out into appropriate nutrient culture media all of the preserved samples grew normally, demonstrating rapid and complete reversibility of the bacteriostatic effect.

Methods of Treating Chronic Rhinosinusitis and Use of Boric Acid Formulations for Treating CRS Boric acid is a very mild and well-tolerated topical bacteriostatic and fungistatic agent with very low potential for induction of microbial resistance in human pathogens. Whether applied in dilute solution or ointment form on skin, or used in pure form on vaginal epithelium, boric acid shows little or no evidence of tissue irritation or other adverse events in human subjects. Topical boric acid is not significantly absorbed across uninjured skin or vaginal epithelium; thus, the potential for systemic exposure via topical applications to the paranasal epithelium may be correspondingly low.

The present invention is based on a demonstration that the underlying cause and symptoms of microbial-related CRS disease can be ameliorated by intranasal delivery of a dilute boric acid solution followed by exsufflation and/or expectoration to clear mucus and excess boric acid solution from the nasal and paranasal sinuses. The method comprises administering a formulation of boric acid to the nasal and paranasal cavities of a patient in need. The present invention also provides for use of a formulation comprising boric acid for the treatment of chronic rhinosinusitis in a subject in need.

In either the method or use described and claimed herein, the formulation may comprise boric acid in an amount (weight per volume, w/v) from about 1.0-4.0%, particularly from about 1.0-2.5%. In particular embodiments, the formulation comprises boric acid in an amount of about 2.0% (w/v). The solvent for the formulation may be any solvent having suitable characteristics of flowability for sufficient nasal and paranasal access, and compatibility with boric acid. An exemplary solution that satisfies these requirements is a saline solution, wherein the concentration (w/v) of sodium chloride (NaCl) in water is from about 0.5-1.2%. In a particular embodiment the concentration of sodium chloride in water is 0.9% (w/v), that is, isotonic saline. In one embodiment, the formulation comprises about 2% (w/v) of boric acid in a saline solution having about 0.9% (w/v) of sodium chloride in water. Alternative solvents having characteristics similar to those of a saline solution as described above may be used in the present formulations and are specifically encompassed by the present invention.

The formulation may be of a pH that is a natural result of formulating the desired amount of boric acid in an appropriate solvent, such as a saline solution.

The method of administering the boric acid formulation generally comprises applying a volume of the formulation into each nare of the patient in a manner sufficient to penetrate the nasal and paranasal cavities. The volume of the formulation may be administered by any appropriate means known to those skilled in the art and include, but are not limited to douching, nebulization, atomization, inhalation, irrigation, spray, drops, or insufflations. In particular embodiments, a volume of the formulation is administered by drops into each nare. In another particular embodiment, the volume of the formulation is applied by spray into each nare. The invention specifically includes an embodiment wherein the formulation is a sterile, aqueous isotonic suspension or solution of boric acid administered intranasally to the nasal-paranasal mucosa via spray pump. The various methods of administration may be and often are accompanied by maneuvering the head, and thereby the nasal and paranasal cavities, in a manner sufficient to distribute the formulation throughout the nasal and paranasal cavities. The method also may and often does include a subsequent step of clearing the nasal and paranasal cavities of excess formulation by expectoration and/or exsufflation.

The volume of the formulation administered into each nare may vary but in all cases should be a volume sufficient to coat the nasal and paranasal cavities. In particular embodiments, the volume administered to each nare is about 1-2 mL. Administration is generally based on need and may be repeated several times per day while symptoms are present. In particular embodiments, formulation is administered to the subject in need 1-3 times per day.

A subject in need is a subject having symptoms consistent with chronic rhinosinusitis. In some embodiments, the subject has been diagnosed as having chronic rhinosinusitis. The subject having chronic rhinosinusitis may also have nasal polyps (CRSwNP) or be without nasal polyps (CRSsNP). In particular embodiments, the chronic rhinosinusitis is microbial-related CRS. In some embodiments, the chronic rhinosinusitis is bacterial-related. In some embodiments, the chronic rhinosinusitis is fungal-related.

EXAMPLES

The invention is further understood by reference to the following example, which is intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description. Such modifications fall within the scope of the appended claims.

The subject of the present example is a male who first presented with symptoms of chronic rhinosinusitis in 1987. The subject was subsequently diagnosed with CRSwNP. No allergen was identified as a causative agent. Endoscopic surgery for removal of nasal polyps in 1987 was followed by a short course of antibiotics and several systemic administrations of corticosteroids. A second surgery was required in December 1996 to remove recurring nasal polyps. This surgery was followed up with a short course of oral antibiotics and daily intranasal corticosteroid (INS) therapy. The subject continued on INS therapy for about two years, but with very little tangible relief of recurrent nasal congestion.

In 2012, the subject felt very distinctly like nasal polyps were once again recurring, i.e., the ball-valve sensation always from the same side and especially when lying on one side. Upon this reoccurrence, the subject prepared a sterile formulation of isotonic saline solution containing 2% (w/v) of boric acid (Sigma catalog no. 15663; BioUltra grade (>99.5%) assayed for <5 ppm of individual heavy metals). The formulation was transferred into soft plastic squeeze bottles that originally contained commercial saline for intranasal use.

The subject initially applied 1-2 mL of the boric acid formulation to each nare about 2-3 times per day, tilting his head back to allow thorough irrigation of the sinuses and drainage into his mouth. After each separate irrigation event, the subject expectorated, rinsed his mouth with fresh water, and blew his nose (exsufflated) to expel mucus.

Remission of the subject's CRS symptoms was rapid and profound. During the first day or two of treatment, copious amounts of yellow ropy mucus were expelled, followed by several more days of colorless and less viscous mucus discharge. Within the first week, the subject was able to breathe normally through his nasal sinuses for most of the day. Within three weeks of 2-3 treatments per day, the subject was free of the sensation of nasal congestion and was able to breathe normally full-time. Administration of the boric acid formulation was then reduced to "as-needed."

A recent study of the bacterial constituents of the subject's nasal mucus by light microscopy at 1000×-1500× magnification was performed. The experiments consisted of boric acid lavages that were timed appropriately for before-and-after estimations of bacterial content from a "sneeze-on-a-slide." test. The results were qualitatively clear that (1) the paranasal microbiome consisted mainly of (unidentified) cocci, (2) boric acid lavages acutely reduced the bacterial count dramatically, and (3) the microbiota was substantially replenished within 24-48 hours of boric acid lavage.

Over the past 3 year treatment period, the subject has continued to use this treatment on an "as-needed" basis, typically anywhere from 1-2 times daily to 2 times per week, depending on symptoms. The following is a summary of quality-of-life benefits that have accrued since initiation of treatment for CRSwNP with 2% boric acid in saline:

The subject is no longer a "mouth-breather," and has been able to breathe normally through his nose for the past three years.

The annoying "ball-valve" sensation that the subject feared might signal the return of nasal polyposis completely ceased within a few months of self-treatment initiation.

Within a month or so of treatment initiation, the subject was able to sleep comfortably without the aid of a dental appliance for the first time in approximately a decade. Episodes of snoring and explosive episodes of sleep apnea have diminished or ceased entirely.

The subject's sense of smell returned to an astonishing degree within the first year or so of treatment.

Although the subject has had a few colds over the past 3 years, he has not experienced any painful acute sinus infections since beginning treatment with boric acid.

The subject also reports that the frequency and severity of occasional headaches has decreased over the past 3 years of CRS self-treatment.

Various modifications of the invention, in addition to those shown and described herein, will become apparent to those skilled in the art from the foregoing description. Such modifications are intended to fall within the scope of the appended claims.

All references cited herein are hereby incorporated by reference herein in their entirety.

What is claimed is:

1. A formulation consisting essentially of an aqueous saline suspension or solution of boric acid for use in treating chronic rhinosinusitis, wherein the boric acid is at a concentration of about 2.0-4.0% (w/v) and the aqueous saline suspension or solution consists of 0.5-1.2% (w/v) sodium chloride in water.

2. The formulation of claim 1, wherein the aqueous saline suspension or solution consists of about 0.9% (w/v) sodium chloride in water.

* * * * *